United States Patent [19]

Wienck et al.

[11] Patent Number: 4,682,506
[45] Date of Patent: Jul. 28, 1987

[54] AUTOMATIC MATERIAL SAMPLER

[75] Inventors: Dennis A. Wienck; Danny K. Mints, both of Duncan, Okla.

[73] Assignee: Halliburton Company, Duncan, Okla.

[21] Appl. No.: 795,394

[22] Filed: Nov. 6, 1985

[51] Int. Cl.$^4$ ............................................. G01N 1/02
[52] U.S. Cl. .............................. 73/863.54; 73/863.56
[58] Field of Search ........... 73/863.41, 863.51, 863.53, 73/863.54, 863.55, 863.57, 863.81, 863.82, 863.86, 864.73, 856, 863.56

[56] References Cited

U.S. PATENT DOCUMENTS

| | | | |
|---|---|---|---|
| 3,005,347 | 10/1961 | Smithson | 73/863.55 |
| 3,659,461 | 5/1972 | Thompson | 73/863.54 |
| 3,690,179 | 9/1972 | Olson | 73/863.56 |
| 4,055,088 | 10/1977 | Diss | 73/863.56 |
| 4,082,004 | 4/1978 | Weber et al. | 73/863.54 |
| 4,120,203 | 10/1978 | Clements et al. | 73/863.54 |
| 4,170,900 | 10/1979 | Ozawa | 73/863.56 |
| 4,538,472 | 9/1985 | Skarpness | 73/863.55 |

OTHER PUBLICATIONS

Brochure from Gustafson, Inc.
Brochures from InterSystems Industrial Products, Inc.
Brochure from Quality Control Equipment Company.

*Primary Examiner*—Jerry W. Myracle
*Assistant Examiner*—Robert R. Raevis
*Attorney, Agent, or Firm*—Joseph A. Walkowski; E. Harrison Gilbert, III

[57] ABSTRACT

An automatic material sampling apparatus includes a housing for receiving a positively or negatively pressurized flow of material to be sampled as the material flows through a conduit, wherein the housing is disposed in-line with the conduit. The apparatus also includes a sampler mechanism for collecting a full cross-sectional sample of the material as the material flows through the housing under positive or negative pressure. The sampler means includes a collection member for receiving the sample and a movement mechanism for moving the collection member to collect or sweep out the full cross-sectional sample of the material. Movement of the collection member can be linear, arcuate or rotational or a combination of directions in different described embodiments of the apparatus.

8 Claims, 23 Drawing Figures

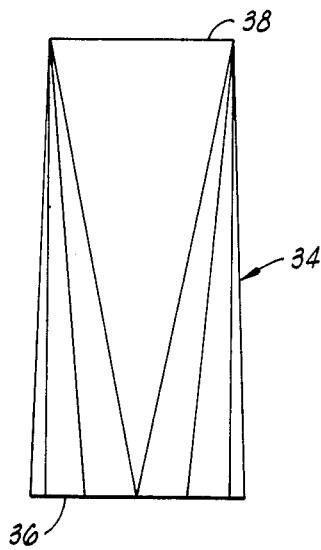
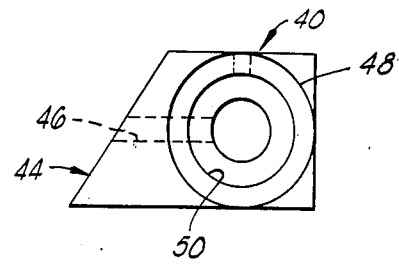
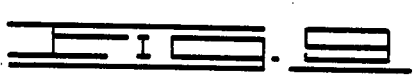
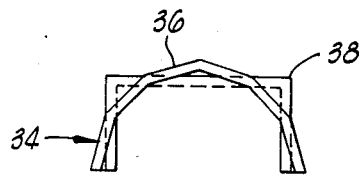
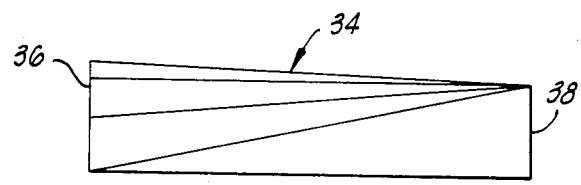
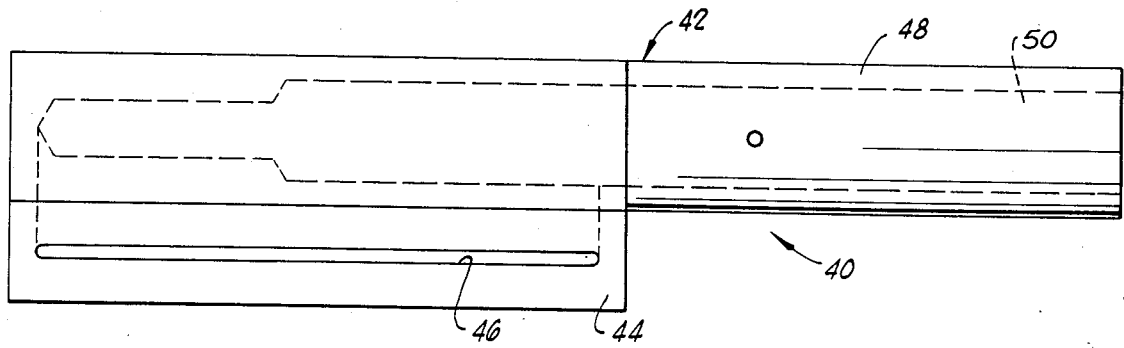
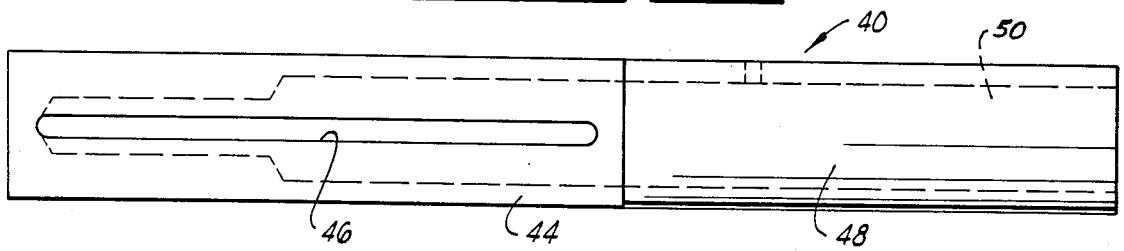

AUTOMATIC MATERIAL SAMPLER

BACKGROUND OF THE INVENTION

This invention relates generally to sampling apparatus for gathering a representative sample of flowing material and more particularly, but not by way of limitation, to an automatic sampling apparatus that obtains a full cross-sectional sample within a positively or negatively pressurized (i.e., above or below atmospheric pressure) pipe or duct system.

In blending processes, there is the need for sampling mixed or blended materials, whether the blends are of solids or liquids or a mixture of solids and liquids or a mixture of solids and gases, to know the amounts of the constituent components for controlling quality of the ultimate blend. For example, in making a cement slurry for use during a cementing job at an oil or gas well, the operator of the job needs to monitor the constituents of the blend to insure that the resultant cement slurry has the necessary properties for the particular job. This need is particularly critical when the blend may have segregated layers of constituent elements so that the blend is not homogeneous. In such a case, a full cross-sectional sample of the blend should be taken to obtain portions of all the layers.

Because some blends are conveyed under pressure, such as in a pneumatic flow, there is the further need for such a full cross-sectional sampling to be taken even in such a pressurized environment, thereby necessitating a suitable sealed construction to prevent loss of material and pressure from within the system. That is, there is the need for an apparatus including a sealing structure which allows the sample of material to pass out of the primary flow path without unwanted loss of material or pressure. The need for a sealing structure also exists when the sampling is taken in a negatively pressurized environment, such as in a vacuum conveyance system.

Several automatic sampling apparatus have been marketed or contemplated. Some are for gravity-flow systems and others are for pressurized systems. Some utilize a sample-taking element fixed in the flow stream and others utilize retractable elements. Some elements are movable across the flow path to take a full cross-sectional sample, but these are not known to be for use in above-atmospheric or below-atmospheric pressure systems. Additionally, at least one of these incorporates a scoop-like element which effectively impedes or otherwise adversely affects the primary flow. Another has a diverting flow line incorporating valves and actuators to open an alternate flow path through which to collect a sample; this type is relatively expensive because of the valves and actuators required, and it is also difficult to clean.

Despite these other types of automatic material samplers, we believe there is a need for an automatic sampling apparatus which can take a full cross-sectional sample of a material flowing under a greater or less than atmospheric pressure without significantly adversely affecting the primary flow, whereby more accurate and reliable samples can be collected from such a a pressurized flow system. Such accuracy and reliability are particularly important where the samples are being used to monitor flows within systems for producing complex blends, such as for producing complex cement slurries at a well site. Improved accuracy and reliability would, in general, provide an important competitive advantage. Such improved sampling makes the blending process more cost effective. To further enhance the cost effectiveness, it is desired that such an apparatus which meets the aforementioned needs also be less expensively constructed than previously known types of sampling apparatus.

SUMMARY OF THE INVENTION

The present invention meets the aforementioned needs and overcomes the shortcomings of the prior art known to us by providing a novel and improved automatic sampling apparatus which collects a full cross-sectional sample even within a "pressurized" (as generally used herein, "pressurized" or the like will refer to a non-atmospheric pressure, i.e., a positive pressure greater than atmospheric pressure or a negative or evacuated pressure less than atmospheric pressure) system, thereby enhancing the accuracy and reliability of the sample test. The present invention is relatively inexpensive to construct. Furthermore, operation of the present invention does not significantly adversely affect the primary flow of material.

Broadly, the apparatus of the present invention comprises housing means for receiving therethrough a flow of the material as the material flows through a conduit. The apparatus also includes sampler means, connected with the housing means, for collecting a full cross-sectional sample of the material as the material flows through the housing.

The sampler means includes a collection member disposed in the housing means, and the sampler means further includes movement means for moving the collection member, from a location outside the full cross-sectional sample area of the material, across the full cross-sectional sample area of the flow of material.

The housing means includes cross-section defining means for defining the cross-sectional sample area across which the collection member is movable. The cross-section defining means has receptacle means for receiving the collection member outside the defined cross-sectional sample area when the collection member is moved thereto by the movement means. The housing means further includes connector means for connecting the cross-section defining means to the conduit through which the material flows so that the crosssectional sample area defined by the cross-section defining means is aligned with the cross section of the conduit.

Therefore, it is a general object of the present invention to provide a novel and improved automatic sampler apparatus. Other and further objects, features and advantages of the present invention will be apparent to those skilled in the art when the following description of the preferred embodiments is read in conjunction with the accompanying drawings.

BRIEF DESCRIPTION OF THE DRAWINGS

FIG. 9 is a plan view of a portion of an adapter member of the first preferred embodiment.

FIG. 10 is an end elevational view of the portion of the adapter member shown in FIG. 9.

FIG. 11 is a side elevational view of the portion of the adapter member shown in FIG. 9.

FIG. 12 is a plan view of a collection member of the first preferred embodiment.

FIG. 13 is a front elevational view of the collection member of the first preferred embodiment.

FIG. 14 is an end elevational view of the collection member of the first preferred embodiment.

DETAILED DESCRIPTION OF THE PREFERRED EMBODIMENTS

Several embodiments of an automatic sampling apparatus constructed in accordance with the present invention have been contemplated. Broadly, each of these embodiments includes housing means for receiving a pressurized (as previously defined, either positively or negatively pressurized) flow of the material to be sampled as it flows through a conduit, such as a pipe or duct, into which the apparatus is connected in an in-line or aligned configuration (i.e., the apparatus becomes part of the primary flow path of the flowing material). The present invention also includes sampler means for collecting a full cross-sectional sample of the material as the material flows through the housing means under pressure. The sampler means includes a collection member disposed in the housing means, and it further includes movement means for moving the collection member, from a location outside the full cross-sectional flow sample area of the material, across the full cross-sectional, pressurized flow sample area of the material. The housing means includes cross-section defining means for defining the cross-sectional sample area across which the collection member is movable, and it also includes connector means for connecting the cross-section defining means to the conduit so that the cross-sectional sample area defined by the cross-section defining means is aligned with the cross section of the conduit. These general elements of the present invention will be more particularly described with reference to the drawings which disclose three principal alternative embodiments, two of which are shown with specific alternative components.

A first preferred embodiment is illustrated in FIGS. 1-17. Because the housing means of the present invention is inserted into the flow path of the material to be sampled, the housing means can be said to define a flow path insert means for inserting the apparatus into the line through which the material to be sampled flows. In this first preferred embodiment, this housing means, or flow path insert means, includes a sampling window member 2 and receptacle means 4 for receiving the collection member in a non-sampling position outside the sampling window defined by the sampling window member 2. The elements 2, 4 define the cross-section defining means of the first preferred embodiment. Adapter means is used in this embodiment as the connector means for connecting the sampling window member 2 and receptacle means 4 into the line through which the material to be sampled flows.

Figure 7:
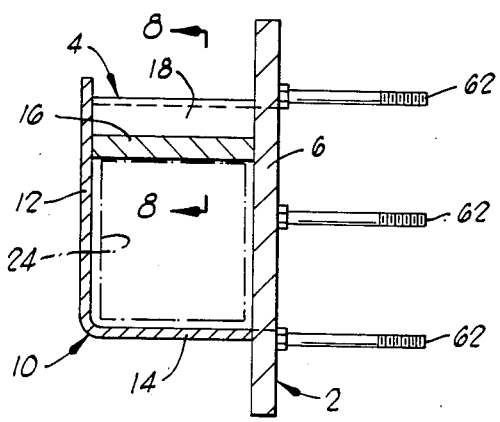
FIG. 7 is a cross-sectional end elevational view, taken along line 7—7 in FIG. 4, of a cross-section defining means of the housing means of the first preferred embodiment.

The sampling window member 2 of the first preferred embodiment is particularly shown in FIG. 7. The member 2 includes a rectangular outlet plate 6 defining a side wall of the member 2. The plate 6 has a slot 8 defined therein. The slot 8 is elongated and has a notch or key portion 9 at the top for receiving the collection member as subsequently described hereinbelow; however, the portion 9 may be deleted when the collection member is constructed so that it can be manipulated or otherwise moved through a straight slot. In the preferred embodiment the slot 8 extends parallel to the height of a rectangular area defined within the sampling window member 2. Stated differently, the slot 8 extends transversely to the width of such retangular area. The length of the slot 8 is not less than the height of the subsequently described sampling window area.

Figure 8:
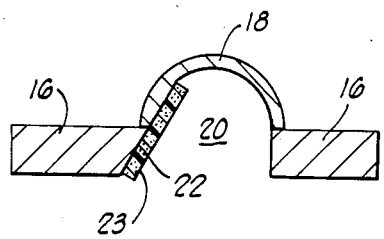
FIG. 8 is a side elevational view, taken along line 8—8 in FIG. 7, of a receptacle means of the first preferred embodiment.

The outlet plate 6 is connected, such as by welding, to an L-shaped bracket 10 having legs defining a side wall 12 and a side wall 14 of the member 2. The side wall 12 extends parallel to the plate 6. The side wall 12 is spaced from the plate 6 by the side wall 14 extending perpendicularly therebetween. Also extending between the side wall 12 and the plate 6 is the receptacle means 4 which in this preferred embodiment includes a bifurcated plate 16 having two portions connected by a semicircular member 18 defining a receptacle 20 having a beveled front surface 22 as shown in FIG. 8. This defines a fourth side wall of the crosssection defining means of this preferred embodiment. Attached to the surface 22 is a seal member 23, such as a foam rubber strip.

The interior surfaces of the elements 6, 12, 14, 16 define a rectangular flow area through which the material to be sampled can flow. Within this area is a rectangular cross-sectional sample area, or sampling window, 24 (see FIG. 7). This area is coextensive with the area swept by an inlet opening in the collection member subsequently described. As in apparent from viewing FIG. 7, the area 24 is substantially the same as the maximum potential flow area of the material; therefore, the present invention is defined as having the capability of obtaining a full cross-sectional sample of the flowing material, wherein "full" is not intended to means necessarily the maximum cross-sectional area, but rather to mean simply an area by which a sufficiently representative sample of the complete flow can be obtained. The area 24 lies within a plane extending perpendicular to the direction of the primary flow of the material to be sampled. Although the area 24 of this embodiment is rectangular, it is contemplated that other cross-sectional shapes can be accommodated by the present invention in varying aspects.

The adapter means by which the cross-section defining means is connected into the line or conduit containing the primary flow of material includes two adapter members 26 and 28. Each adapter member 26, 28 has a transition section 30 having a polygonal end to which is connected a suitable circular coupling element 32, such as a Victaulic clamp nipple. The other end of the transition section 30 has a rectangular opening communicating with the rectangular cross-sectional area 24. In this preferred embodiment the rectangular end of the transition section 30 of the member 26 is welded to the inlet side of the sampling window member 2 and receptacle means 4 combination and the rectangular end of the member 28 is welded to the outlet side of the combination.

In this preferred embodiment the transition section 30 is constructed of two similar half-sleeve members, one of which is shown in FIGS. 9–11 and identified by the reference numeral 34. FIGS. 9–11 show that each member 34 has one polygonal forming end 36 and one rectangular forming end 38. These shapes are used to adapt this embodiment for use in circular conveying lines of types normally used for pneumatically or otherwise conveying materials of the type to be sampled by the present invention. The circular cross section of such a line is converted into the rectangular cross section including the area 24 through which the collection member of the sampler means of this embodiment can be readily moved for obtaining a full cross-sectional sample of the flowing material.

The collection member of the preferred embodiment shown in FIGS. 1–17 is particularly illustrated in FIGS. 12–14. This member is generally identified in these drawings by the reference numeral 40. The member 40 includes a body 42 having a beveled or angular inlet face or surface portion 44 in which inlet means is defined for receiving as a sample a portion of the flowing material. In this embodiment the inlet means includes an elongated slot 46; however, other types of openings, such as multiple slots or holes, may be used. The slot 46 extends laterally across the width of the cross-sectional area 24, and thus transversely to the flow of material, when the member 40 is disposed in the cross-section defining means such as is illustrated in FIG. 15.

The body 42 of the preferred embodiment is elongated so that it presents only a small cross-sectional obstruction in the primary flow path whereby the primary flow is not substantially adversely affected when the body 42 is moved within the sampling cross-sectional area. This elongated body extends longitudinally from the face portion 44 into a neck portion 48 having a central bore defined therethrough in communication with the slot 46. The neck portion 48 terminates in an outlet opening 50 to which a flow line 52 (FIGS. 1 and 2) is connected.

The flow line 52 is a hose or other suitable tubing or the like having an interior channel or opening through which the collected sample can be conveyed from the collection member 40 to a sample collecting container or jar 54. Associated with the jar 54 in the first illustrated embodiment is a dust filter 56 through which air collected with the sample is filtered by a paper filter and vented to atmosphere. It is contemplated that a suitable purging apparatus can be used with or incorporated in this embodiment for purging the dust filter 56.

Figures 1, 2:
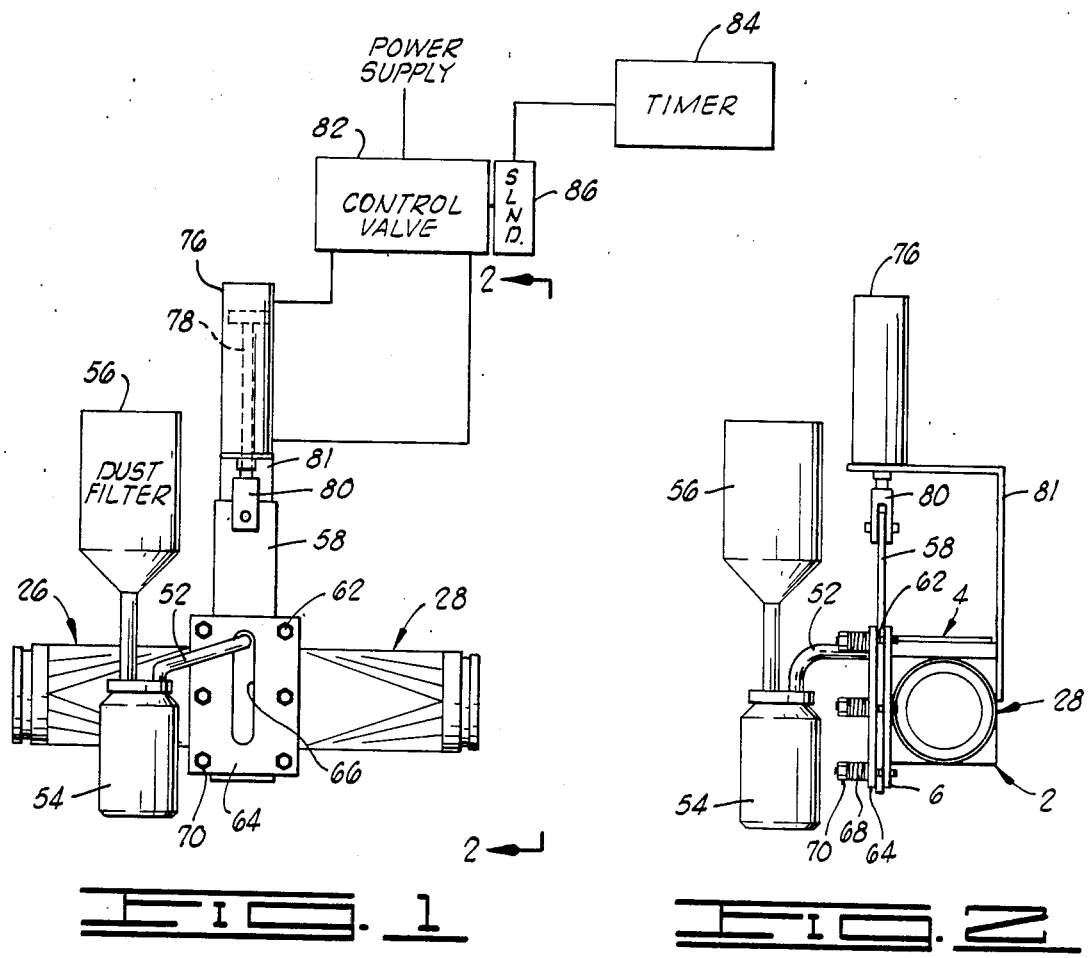
FIG. 1 is a functional block and schematic diagram of a first preferred embodiment of the present invention.
FIG. 2 is a elevational view of a portion of the embodiment shown in FIG. 1 as taken along line 2—2.
Figure 3:
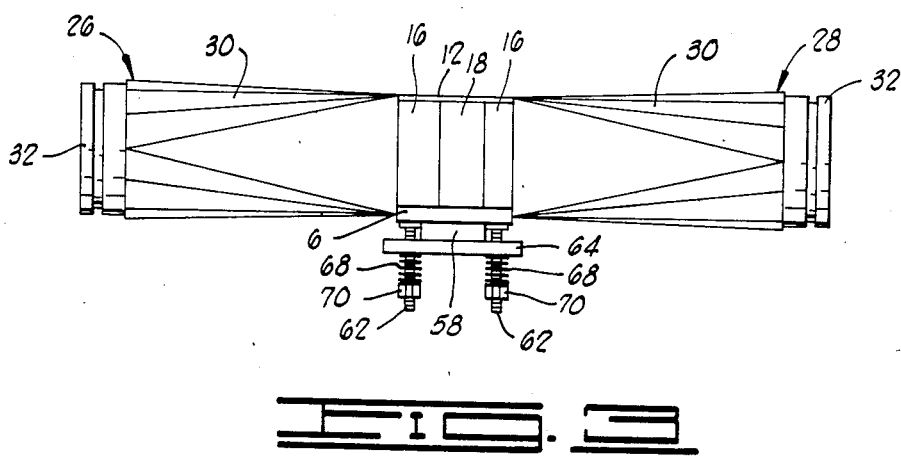
FIG. 3 is a plan view of a housing means of the first preferred embodiment.
Figure 4:
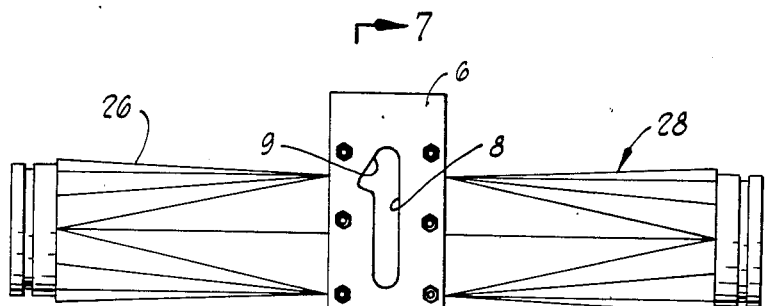
FIG. 4 is a side elevational view of the housing means of the first preferred embodiment.
Figure 5:
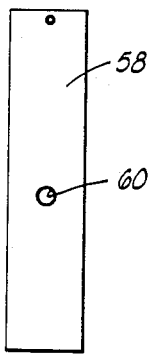
FIG. 5 is an elevational view of a seal plate of the first preferred embodiment.
Figure 15:
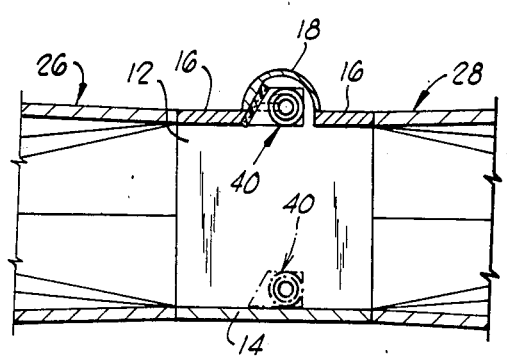
FIG. 15 is a sectional elevational view showing the relationship between the collection member and the cross-section defining means of the first preferred embodiment.

In its assembled combination, the collection member 40 is disposed within the cross-section defining means as illustrated in FIG. 15. The neck portion 48 extends therefrom through the slot 8 to the flow line 52 which extends to the sample jar 54 as shown in FIGS. 1 and 2. Because the interior of the cross-section defining means, which includes the cross-sectional sample area 24, is pressurized in that it is in communication with the pressurized conduit through which the material to be sampled is primarily flowing, the preferred embodiment must include a suitable pressure seal by means of which the slot 8 can be sealed around the neck portion 48 so that material and pressure do not escape from or enter into the hollow interior of the housing means. In this embodiment, such seal means includes a seal plate 58 and means for retaining the seal plate 58 in sealing engagement with the plate 6 of the sampling window member 2. The seal plate 58 is best viewed in FIGS. 3 and 5, wherein the seal plate 58 is shown to be a rectangular plate having a central circular aperture 60 defined therethrough. The aperture 60 has an inner diameter substantially the same as the outer diameter of the neck portion 48 of the collection member 40, or it is otherwise constructed to provide a suitable seal between the plate 58 and the neck portion 48. The plate 58 is disposed adjacent the plate 6 between a plurality of outwardly extending bolts 62. In the preferred embodiment the seal plate 58 is made of any suitable substance which will establish a movable pressure seal adjacent the slot 8. For example, ultra-high molecular weight (UHMW) polyethylene provides a suitable abrasion-resistant substance of which the seal plate can be made.

Figure 6:
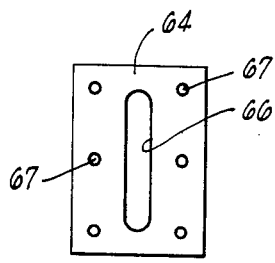
FIG. 6 is an elevational view of a retaining plate of the first preferred embodiment.

The means for retaining the seal plate 58 adjacent the plate 6 includes one of two alternate constructions in the illustrated preferred embodiment. One of these alternatives includes a rectangular retaining plate 64 having an elongated slot 66 defined therein as shown in FIG. 6. Along the periphery of the retaining plate 64 are six apertures 67 disposed for receiving the bolts 62. The retaining means also includes springs 68, each of which is mounted on a respective one of the bolts 62 and retained thereon by suitable fastening means, such as by a respective one of a plurality of nuts 70. The springs 68 and nuts 70 define biasing means for urging the retaining plate 64 against the seal plate 58.

Figure 16:
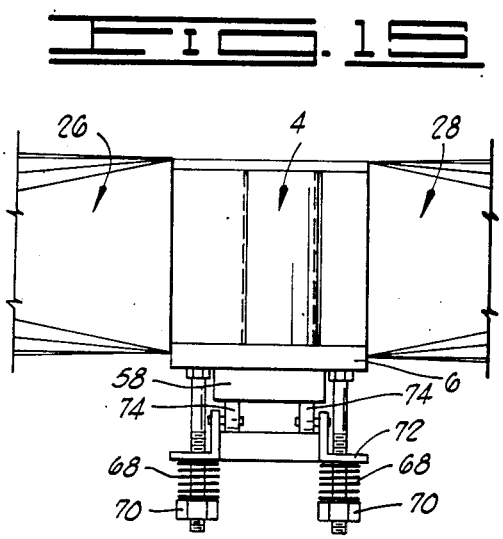
FIG. 16 is a plan view of a part of the first preferred embodiment housing means having an alternative sealing structure associated therewith.
Figure 17:
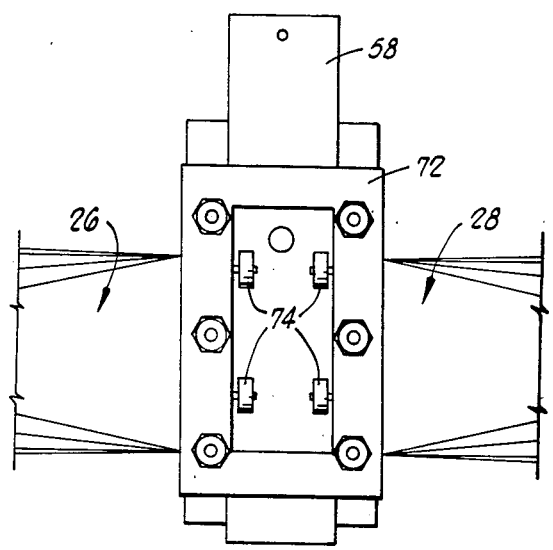
FIG. 17 is a side elevational view of the alternative sealing structure shown in FIG. 16.

The other alternative construction of the retaining means is shown in FIGS. 16 and 17. In this alternative construction, a retaining plate constructed as a roller bracket 72 has a plurality of rollers or cam followers 74 attached thereto. Similar springs 68 and nuts 70 are used to bias the roller bracket and cam rollers against the seal plate 58 as illustrated in FIGS. 16 and 17.

When another suitable material, such as steel, is used instead of UHMW material, the springs 68 may be eliminated because they are used in the illustrated embodiment to compensate for significant thickness changes which can occur in UHMW material with varying temperatures. When an elastomer seal is used, the biasing means may be simply the nuts 70 compressing the seal plate against the outlet plate.

The movement means of the first embodiment, by which means the movable pressure seal and the collection member 40 are moved, includes a piston housing 76 having a piston member 78 slidably disposed therein for linearly moving the seal plate 58, to which plate the piston member 78 is connected by a suitable coupling yoke 80 as shown in FIGS. 1 and 2. The piston housing, or cylinder, 76 is attached to the flow path insert means by a mounting bracket 81 welded thereo as is apparent in FIGS. 1 and 2. The elements 76, 78 of the preferred embodiment define a pneumatic drive means operable in response to an air supply controlled through an air control valve 82 which in turn is controlled by an electric timer 84 operating a solenoid 86. These elements are of suitable types as known to the art. Generally, any suitable means of linearly moving the seal plate may be used, including electric actuators, hydraulic cylinders, or mechanically driven devices.

In the illustrated preferred embodiment the electric timer 84 is suitably controlled to actuate the valve 82 whereby the piston member 78 linearly moves the seal plate 58, and thus the flow line 52 and the collection member 40 connected therewith, in a vertical direction for the orientation shown in the drawings, from a retracted or nonsampling position, wherein the collection member 40 is sealingly received in receptacle 20 with the face portion 44 sealed by the seal 23, to a fuly lowered position at the bottom of the rectangular area 24 adjacent the side wall 14 and then back to the fully retracted position, whereby the inlet slot 46 of the collection member 40 is twice swept across the cross-sectional sampling area 24. The timer 84 can be adjusted so that such movement is continuous or so that the movement can be stopped at any suitable location, such as at the bottom of the travel, across the cross section 24. Generally, the timer 84 is to be controlled so that a representative sample from across the cross section of the flowing material is obtained. Although the timer 84 has been described as electric, it is contemplated that a pneumatic or a mechanical timer, or other suitable control mechanism can be used. Such other type might even be selected as an explosion-proof type for use in environments where such a precaution is required.

In this embodiment, it is contemplated that all of the elements but the electric timer will be enclosed in a weatherproof housing for protection. It is contemplated that the electric timer will be positioned in a control room or at a suitable control location to allow convenient operation of the invention at a site spaced from the actual flow.

Reiterating, this operation is achieved by the timer 84 actuating the control valve 82 to move the piston member 78 downward, which moves the seal plate 58 and the flow line 52 and the collection member 40 longitudinally downward relative to the slot 8, and by the timer 84 then controlling the valve 82 to retract the piston member 78 after a sufficient downward movement, which moves the seal plate 58 and the flow line 52 and the collection member 40 upward. FIG. 15 shows the collection member 40 in its fully retracted, or non-sampling, position outside of the rectangular cross-sectional area 24 and the flow path of the material. The downwardmost sampling position of a plurality of possible vertically related sampling positions of the collection member 40 is shown in phantom lines in FIG. 15. Thus, it can be seen from FIG. 15 that the collection member 40 moves vertically across the entire cross-sectional area 24 for receiving through the elongated slot 46 individual, horizontally extending sectors of material ("sector" here referring to the area of the slot 46) which collectively constitute a full cross-sectional sample of the flowing material. Because in the illustrated embodiment the width of the elongated slot 46 is not fully coextensive with the width of the maximum cross-sectional area in the cross-section defining means, as previously mentioned, the use of the word "full" in defining the cross-sectional area across which the sample is taken is intended to indicate a size suitable for receiving a representative portion across the flow without requiring the sample to be taken from every point location within the maximum cross-sectional area of the flow. Although the foregoig describes the first illustrated embodiment, it is contemplated that, in general, embodiments may be constructed wherein the collection member is moved other than in a vertical direction or wherein the retracted position of the collection member is located other than at the top of the housing, for example.

Figure 18:
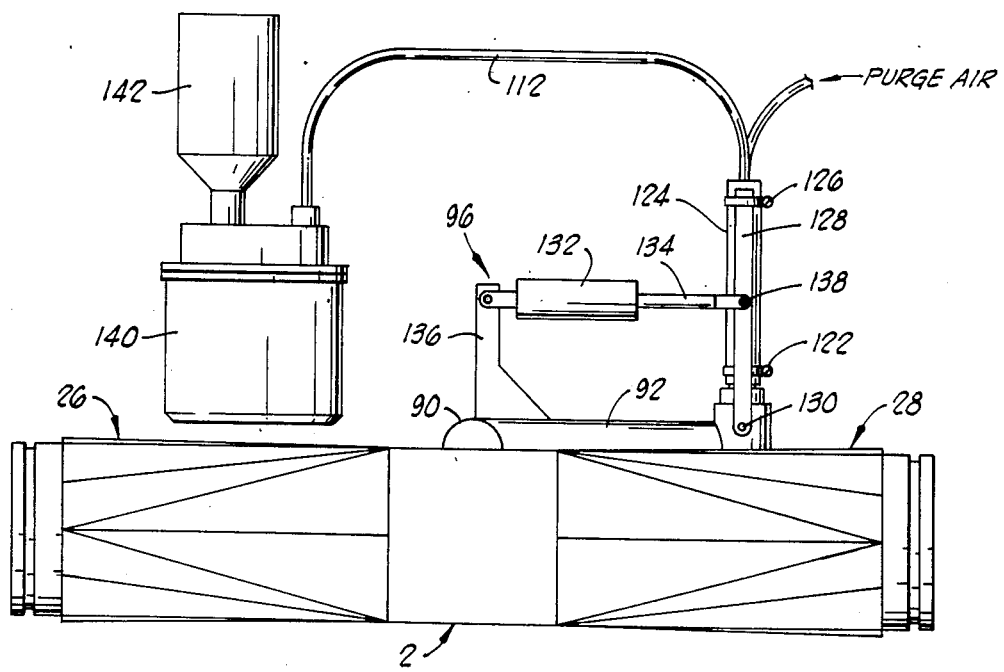
FIG. 18 is an elevational view of a second preferred embodiment of a sampling apparatus of the present invention.
Figure 19:
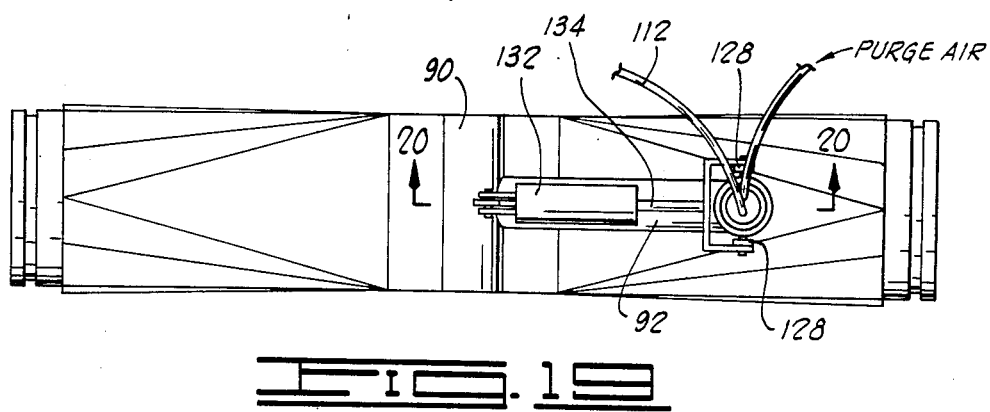
FIG. 19 is a plan view of a portion of the second preferred embodiment shown in FIG. 18.
Figure 20:
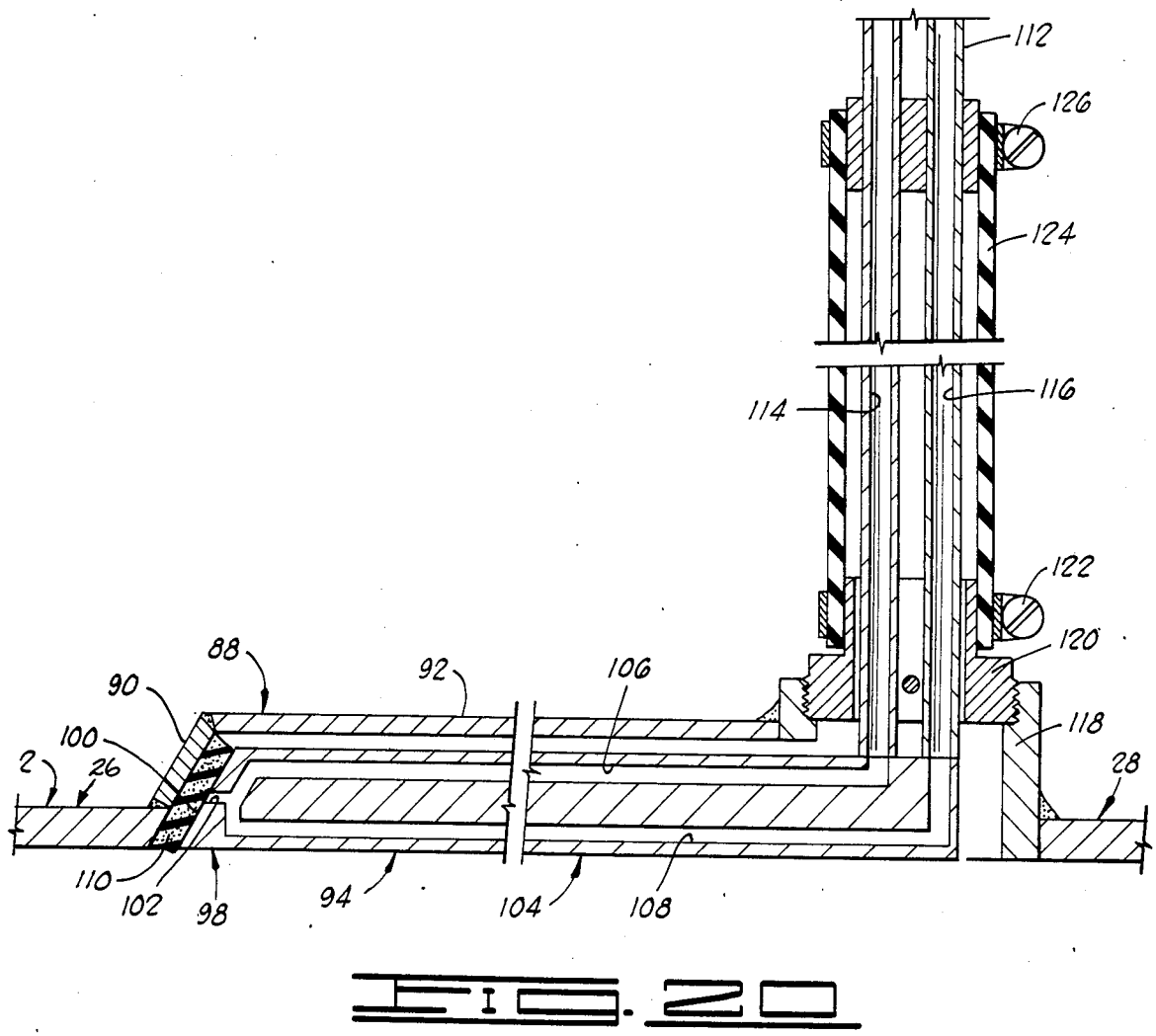
FIG. 20 is a cross-sectional view, taken along line 20—20 in FIG. 19, of a portion of the housing means and collection member of the second preferred embodiment.
Figure 21:
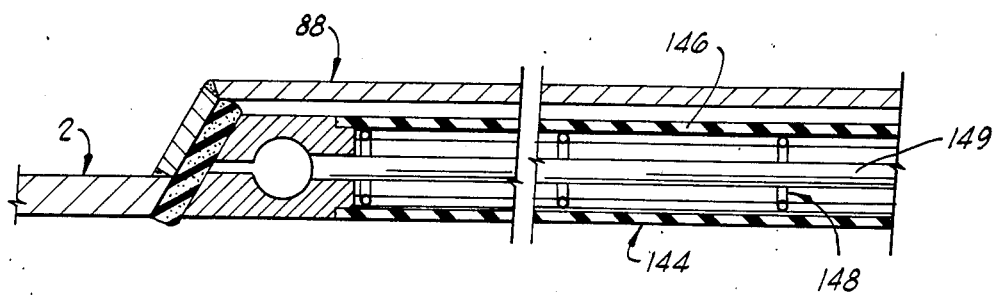
FIG. 21 is an illustration of another embodiment of a collection member for use as an alternative in the second preferred embodiment shown in FIGS. 18-20.

A second preferred embodiment of the present invention is shown in FIGS. 18–20, with an alternative construction of another type of collection member which can be used in the second embodiment shown in FIG. 21. The housing means of the second embodiment is substantially the same as that for the first embodiment except for the receptacle means, the second embodiment including a sampling window member 2 and adapter members 26, 28 substantially corresponding to those of the first embodiment. In the second embodiment the receptacle means includes a larger protuberant portion 88 for receiving the collection member of the second embodiment in its retracted position. In particular, the receptacle means includes a head receiving portion 90 which is similar to the member 18 of the first described embodiment, and it also includes a neck receiving portion 92 extending transversely from the head receiving portion 90 longitudinally along a portion of one of the adapter members otherwise constructed similarly to the corresponding adapter members 26, 28 in the first-described embodiment, as indicated by the use of the same reference numerals.

Aside from the receptacle means, the principal difference in the second preferred embodiment is the construction of the sampler means which in this embodiment includes a collection member 94 and movement means 96.

The collection member 94 has a rigid body including an inlet or head portion 98 having a beveled or angular frontal or inlet face 100 in which an elongated slot 102 is defined (as mentioned hereinabove with reference to the first embodiment, other suitable inlet means may be used). The head portion 98 is similar to the corresponding portion 44 of the collection member 40. In this embodiment of the collection member 94, however, a neck portion 104 extends perpendicularly from a central location of the head portion 98, as opposed to extending longitudinally from the end of the head portion as in the first-described embodiment. The neck portion 104 is constructed so that a sample flow channel 106 and a separate purge channel 108 are defined therethrough as shown in FIG. 20. Both of these channels communicate with the inlet slot 102 so that the sample is received through the sample flow channel 106 and so that purge air can be applied to the slot 102 through the channel 108 for purposes of cleaning the slot 102. When the collection member 94 is in its retracted position, as shown in FIG. 20, the inlet face is sealingly engaged with a suitable seal member 110, such as a foam rubber strip attached to the beveled wall of the receptacle means.

Extending transversely from the end of the neck portion 104 opposite the head portion 98 is a rigid portion of a flow line 112 having two channels 114, 116 defined therethrough respectively communicating with one of the channels 106, 108 in the collection member 94. The flow line 112, which forms another part of the sampler means of the second embodiment, exits portion 92 of the receptacle means through a collar 118 having an adapter 120 threadedly connected thereto. Connected to the adapter member 120 by a suitable clamping mechanism 122 is one end of a flexible boot or hose 124. The boot 124 (flexible casing) has its opposite end sealingly connected to the outer periphery of the flow line 112 by a suitable clamping mechanism 126. These elements define, as another part of the sampler means of the second embodiment, a sealing means for sealing the exit of the flow line 112 from the receptacle means so that material and pressure within the housing means of the present invention, and the conduit into which it is connected, are not lost.

For supporting the flow line 112 and boot 124, the movement means 96 includes a pivotal brace means including at least one elongated member 128 (two are shown in FIG. 19) having one end attached to the coupled hose 124 and flow line 112 and having another end pivotally connected about a pivot axis 130 to the collar 118 as best viewed in FIG. 18. Forming another part of the movement means 96 is an air cylinder, or piston housing, 132 having a piston member 134 linearly movable therethrough. The cylinder 132 is connected to the housing means by a suitable bracket 136. Actuation of the air cylinder 132 and piston 134, such as by similar mechanisms to those described hereinabove with reference to the first embodiment, pivot the brace member 128 to which the piston 134 is connected at a pivot connection 138.

Connected to the flow line 112 are a suitable container 140 and dust filter 142 of types similar to those described hereinabove with reference to the first embodiment.

Due to the rigid construction of the collection member 94 and at least a portion of the flow line 112 connected thereto and further due to the use of the flexible boot 124, actuation of the air cylinder 132 causes the collection member 94 to pivot so that it moves between its retracted position shown in FIG. 20 and a fully extended position adjacent the bottom of the sampling window member of the cross-section defining means within the housing means of this embodiment. Thus, the sample receiving slot 102 is arcuately swept through an arc which covers an area sufficient to obtain a full cross-sectional sample of the flow of material passing through the rectangular cross-sectional area 24 which is similarly included in the second embodiment.

An alternative embodiment of the collection member 94 is shown in FIG. 21. This construction is generally identified by the reference numeral 144. This member has an outer flexible hose 146 which encloses an adjustable linkage framework 148 forming part of the movement means of this alternative construction. A flow line 149 extends through the hose 146. The adjustable linkage framework 148, which is shown as a pivotable parallelogram structure, is controlled by suitable control wires (not shown) so that the flexible hose 146 can be manipulated to sweep across any of various desired sampling areas. This exemplifies the contemplation that the collection member may be constructed with a single, relatively small opening and that the movement means may be used therewith to move the collection member in a pattern horizontally and vertically (or otherwise) to cover the full cross section of the flow. This can be adapted for use with circular or other shaped cross sections of conveying conduits so that no transition sections, such as in adapter members 26, 28, are needed.

Figure 22:
FIG. 22 is an end elevational view of a third preferred embodiment of the present invention.
Figure 23:
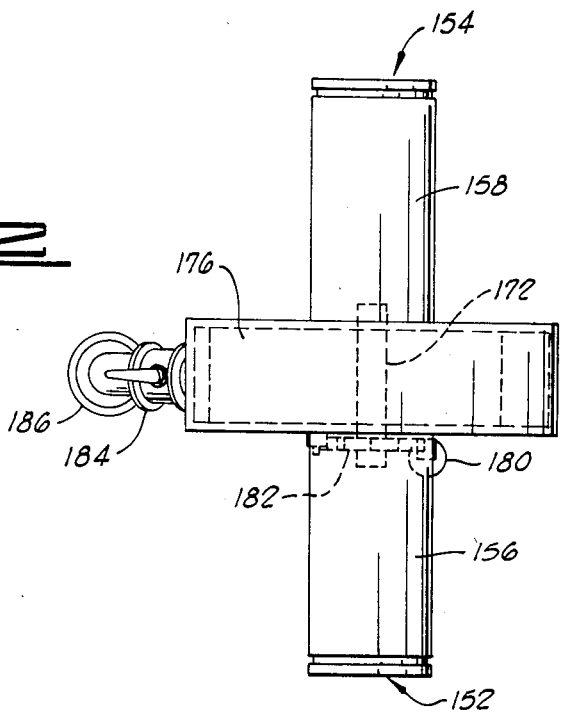
FIG. 23 is a plan view of the third preferred embodiment.

The third embodiment of the present invention is shown in FIGS. 22 and 23. This embodiment defines its flow path insert means with a circular sampling window member 150 having a hollow interior into which an opening 152 and an opening 154 are defined. The opening 152 receives the flow of material and the opening 154 provides an exit for the primary flow of material. These openings are connected into the primary conduit through suitable adapter members 156, 158. Because the sampling window member 150 is much larger in cross section than adapter elements 156, 158 which direct material flow through only a portion thereof offset from the center, there is no need for the adapter elements 156, 158 to provide a circular-to-rectangular transition as in the first two described embodiments.

Rotatably disposed in the sampling window member 150 is a collection member 160 of the third embodiment. The collection member 160 in this embodiment is a vane feeder member having a plurality of vanes 162, 164, 166, 168, 170, 171 affixed to a central shaft 172. Adjacent ones of the vanes define sectors with cross-sectional areas greater than the area of the opening 152 through which the primary flow of material enters the sampling window member 150. This is best shown in FIG. 22 wherein a sector 174 is defined between the vanes 162, 164.

The sampling window member 150 has a cylindrical peripheral side wall 176 which includes an inner surface 178. The vanes 162-171 are suitably sized so that they extend radially outwardly into engagement with the surface 178; however, this engagement is not pressure sealed so that pressure can communicate among the various sectors defined by the vanes whereby there are no pressure differentials across the vanes. In this embodiment each vane includes a non-sealing plastic wiper member 179 affixed to the outer end of a principal structural member of the vane. The wiper member non-sealingly sweeps along the surface 178 to shear out a full cross-sectional sample of the flowing material when the shaft 172 is rotated.

Such shearing out is achieved by rotating the vane feeder member by a suitable means. As illustrated, one embodiment of this means includes an air cylinder 180 which drives a ratchet mechanism 182. Alternatively a rack mechanism can be used as would be readily known to the art. Other suitable rotational mechanisms can be used.

The rotating means of whatever configuration is preferably operated so that only a single vane passes the opening 152 during any one sample because such limited action is all that is needed to obtain a maximum cross-sectional sample of the flowing material. It is to be noted that in this embodiment a "full" cross-sectional sample encompasses the maximum flow cross section. Such a sample is conveyed through a pressurized flow line 184 into a pressurized sample container 186. These elements are constructed for withstanding the pressure within the primary flow in view of the nonsealing construction of the vane members. Therefore, the flow line 184 and the container 186 need to be suitably constructed to withstand the pressure; however, no other pressure sealing construction needs to be implemented other than for providing a rotary seal around the shaft 172. Thus, with this embodiment, a possibly simpler sealing construction can be used than is needed in a sliding seal embodiment such as first described hereinabove.

Regardless of which embodiment is considered, the present invention broadly provides a novel and improved sampling apparatus for obtaining representative, full crosssectional samples of a flowing material, particularly one flowing under a pressure greater or less than atmospheric pressure. Thus, the present invention is well adapted to carry out the objects and attain the ends and advantages mentioned above as well as those inherent therein. While preferred embodiments of the invention have been described for the purpose of this disclosure, numerous changes in the construction and arrangement of parts can be made by those skilled in the art, which changes are encompassed within the spirit of this invention as defined by the appended claims.

What is claimed is:

1. An apparatus for sampling material flowing through a pressurized conduit, comprising:
    housing means for receiving therethrough a pressurized flow of the material as the material flows through the conduit, said housing means including cross-section defining means for defining a full cross-sectional sample area, and connector means for connecting said cross-section defining means to the conduit so that the cross-sectional sample area defined by said cross-section defining means is aligned with the cross-section of the conduit; and
    sampler means, connected with said housing means, for collecting a full cross-sectional sample of the material as the material flows through said cross-section defining means of said housing means under pressure, said sampler means including:
    a collection member disposed in said housing means having an elongated inlet element with inlet means for receiving a portion of the flowing material;
    movement means for moving said collection member from a location outside the full cross-sectional sample area of the material across the full cross-sectional flow sample area of the material, so that said inlet means receives a portion of said flowing material as it passes thereacross; and
    a flow line connected to said collection member, said flow line having a first sample flow channel and a first purge channel defined therein;
    said inlet element of said collection member having a second sample flow channel defined therein in communication with said inlet means and said first sample flow channel, and a second purge channel defined therein in communication with said inlet means and said first purge channel.

2. An apparatus as defined in claim, 1 wherein:
    said cross-section defining means includes an outlet plate having a slot defined therethrough in communication between the interior and exterior of said cross-section defining means, said slot having said collection member disposed therethrough; and
    said sampler means further includes movable pressure seal means for sealing said slot as said collection member moves longitudinally in said slot in response to said movement means, said seal means including:
    a seal plate having an aperture defined therein through which said collection member is received in sealing engagement;
    a retaining member having a slot defined therein through which said collection member is received; and
    biasing means for biasing said retaining member against said seal plate so that said seal plate sealingly engages said outlet plate.

3. An apparatus as defined in claim 2, wherein said retaining member includes roller means for engaging said seal plate.

4. An apparatus as defined in claim 1, wherein said cross-section defining means includes receptacle means for receiving said collection member outside said defined cross-sectional sample area when said collection member is moved thereto by said movement means, and said movement means includes means for pivotally retaining said collection member in said receptacle means so that said collection member is pivotally movable between a first position, wherein said collection member is received in said receptacle means outside said defined cross-sectional sample area, and at least one second position within said defined cross-sectional sample area, wherein said collection member receives a sample of the material flowing through the conduit.

5. An apparatus as defined in claim 4, wherein:
    said collection member includes a rigid body having a channel defined therethrough;
    said sampler means further includes a flow line having a rigid portion connected to said rigid body in communication with said channel, said flow line extending externally of said housing means; and
    said means for pivotally retaining includes pivotal brace means for pivotally supporting said rigid body and said flow line relative to said cross-section defining means.

6. An apparatus as defined in claim 4, wherein said collection member includes a flexible casing.

7. An apparatus for sampling material flowing through a pressurized conduit, comprising:
    substantially cylindrical housing means for receiving therethrough a pressurized flow of the material as the material flows through the conduit, said housing means including cross-section defining means for defining a full cross-sectional sample area in a non-concentric position with respect to the axis of said substantially cylindrical housing means, and connector means for connecting said cross-section defining means to the conduit so that the cross-sectional sample area defined by said cross-section defining means is aligned with the cross-section of the conduit; and
    sampler means, connected with said housing means, for collecting a full cross-sectional sample of the material as the material flows through said cross-sectional defining means of said housing means under pressure, said sampler means including:
    a collection member disposed in said housing means including a shaft disposed substantially along said axis of said housing means and a plurality of vanes connected to said shaft and extending substantially radially therefrom in spaced relation to each other so that any two adjacent vanes define an area which includes the cross-sectional area of the pressurized flow of the material, each of said vanes including a wiper member at the outermost radial extent thereof in contact with the inner substantially cylindrical wall of said housing means;

rotational movement means for rotating the shaft of said collection member whereby said vanes are moved from a location outside the full cross-sectional sample area of the material, across the full cross-sectional, pressurized flow sample area of the material; and sample receiving means including a flow line communicating with the interior of said housing means through the substantially cylindrical wall thereof and located in a circumferentially offset position from said full cross-sectional sample area, and a sample container means for receiving said material from said flow line.

8. A material sampling apparatus, comprising:

an elongated collection member having a collection channel defined therein for receiving a sample of material and including a body having an inlet portion in which an inlet opening is defined transversely to the direction of flow of the material to be sampled, said body further having a neck portion extending from said inlet portion, said inlet and neck portions having said collection channel defined therethrough;

flow path insert means for inserting said apparatus into a line through which the material to be sampled flows, said insert means including:

a sampling window member having a hollow interior including a cross-sectional area defining a sampling window;

adapter means for connecting said sampling window member into the line through which the material to be sampled flows; and receptacle means, communicating with the hollow interior of sampling window member, for receiving said collection member in a non-sampling position outside said sampling window;

a flow line connected to and extending from said neck portion of said collection member and from said flow path insert means;

seal means for providing a pressure seal between said flow line and said flow path insert means, said seal means including a flexible sealing boot coaxially disposed around at least a portion of said flow line; and movement means for moving said collection member between the non-sampling position and a plurality of sampling positions wherein said collection channel receives samples of the material from across the entire sampling window, said movement means including a support member having one end connected to said flow line and having another end pivotally connected to said flow path insert means and means for pivoting said support member, whereby said flow line and said collection member connected thereot pivot, so that said transverse inlet opening moves through a space across which said sampling window is defined.

* * * * *